United States Patent
Claypool et al.

(10) Patent No.: US 7,621,920 B2
(45) Date of Patent: Nov. 24, 2009

(54) ADJUSTABLE CUT GUIDE

(75) Inventors: Jody Claypool, Columbia City, IN (US); Maleata Y Hall, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 89 days.

(21) Appl. No.: 11/151,062

(22) Filed: Jun. 13, 2005

(65) Prior Publication Data
US 2006/0293681 A1 Dec. 28, 2006

(51) Int. Cl.
*A61B 17/58* (2006.01)
(52) U.S. Cl. .......................................... 606/88
(58) Field of Classification Search .................... 606/86, 606/87, 96, 98, 102
See application file for complete search history.

(56) References Cited

U.S. PATENT DOCUMENTS

| | | | | |
|---|---|---|---|---|
| 4,653,488 A | * | 3/1987 | Kenna et al. | 606/88 |
| 5,122,144 A | * | 6/1992 | Bert et al. | 606/88 |
| 5,234,433 A | | 8/1993 | Bert et al. | |
| 5,445,642 A | | 8/1995 | McNulty et al. | |
| 5,474,559 A | * | 12/1995 | Bertin et al. | 606/89 |
| 5,520,695 A | | 5/1996 | Luckman | |
| 5,562,675 A | | 10/1996 | McNulty et al. | |
| 5,653,714 A | | 8/1997 | Dietz et al. | |
| 5,769,855 A | * | 6/1998 | Bertin et al. | 606/88 |
| 5,830,216 A | * | 11/1998 | Insall et al. | 606/88 |
| 5,853,415 A | * | 12/1998 | Bertin et al. | 606/80 |
| 6,056,754 A | * | 5/2000 | Haines et al. | 606/80 |
| 6,746,453 B2 | * | 6/2004 | Deloge et al. | 606/98 |
| 6,926,720 B2 | * | 8/2005 | Castaneda | 606/98 |
| 7,029,477 B2 | * | 4/2006 | Grimm | 606/88 |
| 7,104,997 B2 | * | 9/2006 | Lionberger et al. | 606/88 |
| 2003/0171757 A1 | | 9/2003 | Coon et al. | |

OTHER PUBLICATIONS

Innex™ Knee System Surgical Technique Primary.

* cited by examiner

*Primary Examiner*—Eduardo C Robert
*Assistant Examiner*—Tara R George
(74) *Attorney, Agent, or Firm*—Baker & Daniels LLP

(57) ABSTRACT

An adjustable cut guide for use in resecting the end of a bone. The cut guide of the includes guide slots, the position of which may be adjusted to one of multiple guiding positions that guide a saw in making the anterior, posterior and/or chamfer cuts in the bone. The cut guide includes a base adapted to attach to the end of a bone and including an anterior end and a posterior end. First and second guide housings are coupled to the base and disposed adjacent the opposing anterior and posterior ends, respectively. Anterior and posterior guide members are rotatably coupled to the first and second guide housings, respectively. Each of the anterior and posterior guide members are rotatable about a guide axis and have a guide slot extending therethrough along the guide axis.

23 Claims, 9 Drawing Sheets

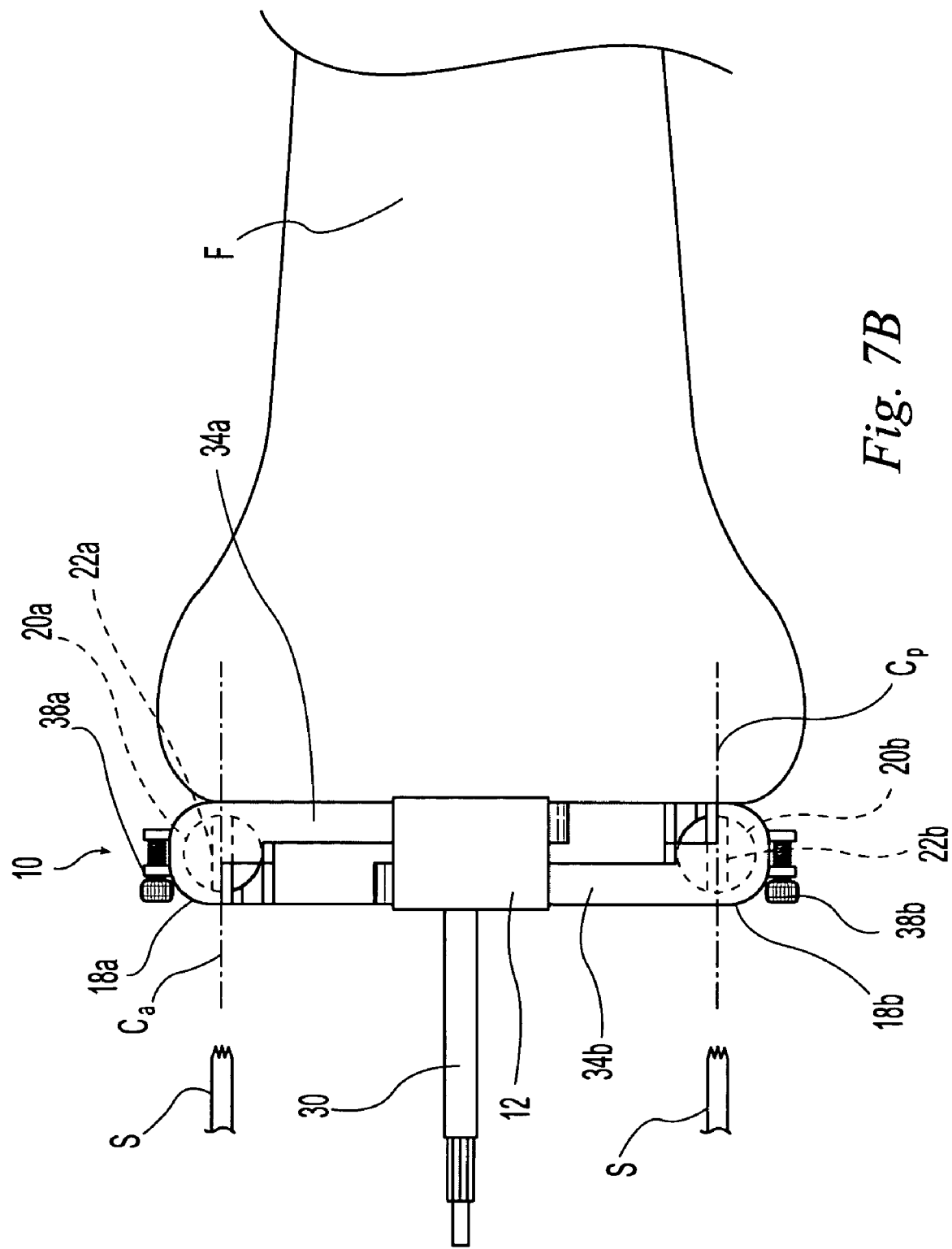

ADJUSTABLE CUT GUIDE

BACKGROUND

The present invention relates to cut guides for resecting the end of a bone and, more particularly, adjustable cut guides for resecting the end of a bone.

Orthopedic procedures for the replacement of all, or a portion of, a patient's joint typically require resecting (cutting) and reshaping of the bones of the joint. For instance, total knee replacement procedures typically involve resecting the distal end of the femur and the proximal end of the tibia prior to implanting the prosthesis components. Resecting the distal end of the femur often involves making several cuts of the distal end of the femur including a distal cut, an anterior cut, a posterior cut, an anterior chamfer cut, and a posterior chamfer cut. The angle and position of these cuts may depend on a variety of factors including the size of the prosthetic component, size of the patient's knee, and conditions of the patient's bone.

Cut guides have been developed to guide the saw and achieve the proper angle and position of these cuts. Conventional cut guides are often in the form of blocks having permanently positioned slots therein for receiving and guiding the saw. Different sized cut guide blocks are provided to correspond to different sized prostheses and to achieve the different cuts. In addition, some cut guide blocks require additional cut accessories to be mounted thereon to provide additional necessary guide slots. Accordingly, making the necessary cuts of the distal end of the femur may require the installation and assembly of multiple cut guide blocks and accessories. In addition, the location and angle of the slots cannot be adjusted once the block is mounted on the femur.

There is a need for an adjustable cut guide that can be used to guide a saw in making the anterior, posterior and chamfer cuts.

SUMMARY

The present invention provides an adjustable cut guide for use in resecting the end of a bone. The adjustable cut guide of the present invention includes guide slots, the position of which may be adjusted to one of multiple guiding positions to guide a saw in making the anterior, posterior and/or chamfer cuts in the bone.

In one form, the adjustable cut guide of the present invention includes a base adapted to attach to the end of a bone. The base includes an anterior end and an opposite posterior end. First and second guide housings are slideably coupled to the base and disposed adjacent the opposing anterior and posterior ends, respectively, of the base. Anterior and posterior guide members are rotatably coupled to the first and second guide housings, respectively. Each of the anterior and posterior guide members are rotatable about a guide axis and have an elongate guide slot extending therethrough along the guide axis. When the base is attached to the end of the bone, the anterior guide member is positioned proximal an anterior side of the bone and the posterior guide member is positioned proximal a posterior side of the bone.

In one aspect, the anterior and posterior guide members are cylindrical in shape. The cut guide may include an intramedullary rod adapter, which has at least one rod opening and is slideably disposed within an adapter slot defined in the base. Each of the guide housings may be slideably coupled to the base such that a distance between each of the anterior and posterior guide members and the base member is adjustable. The cut guide may also include a guide member adjustment device adapted to rotate the guide member about the guide axis.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 7B is a side view of the knee and adjustable cut guide of FIG. 7A;

Figure 1:
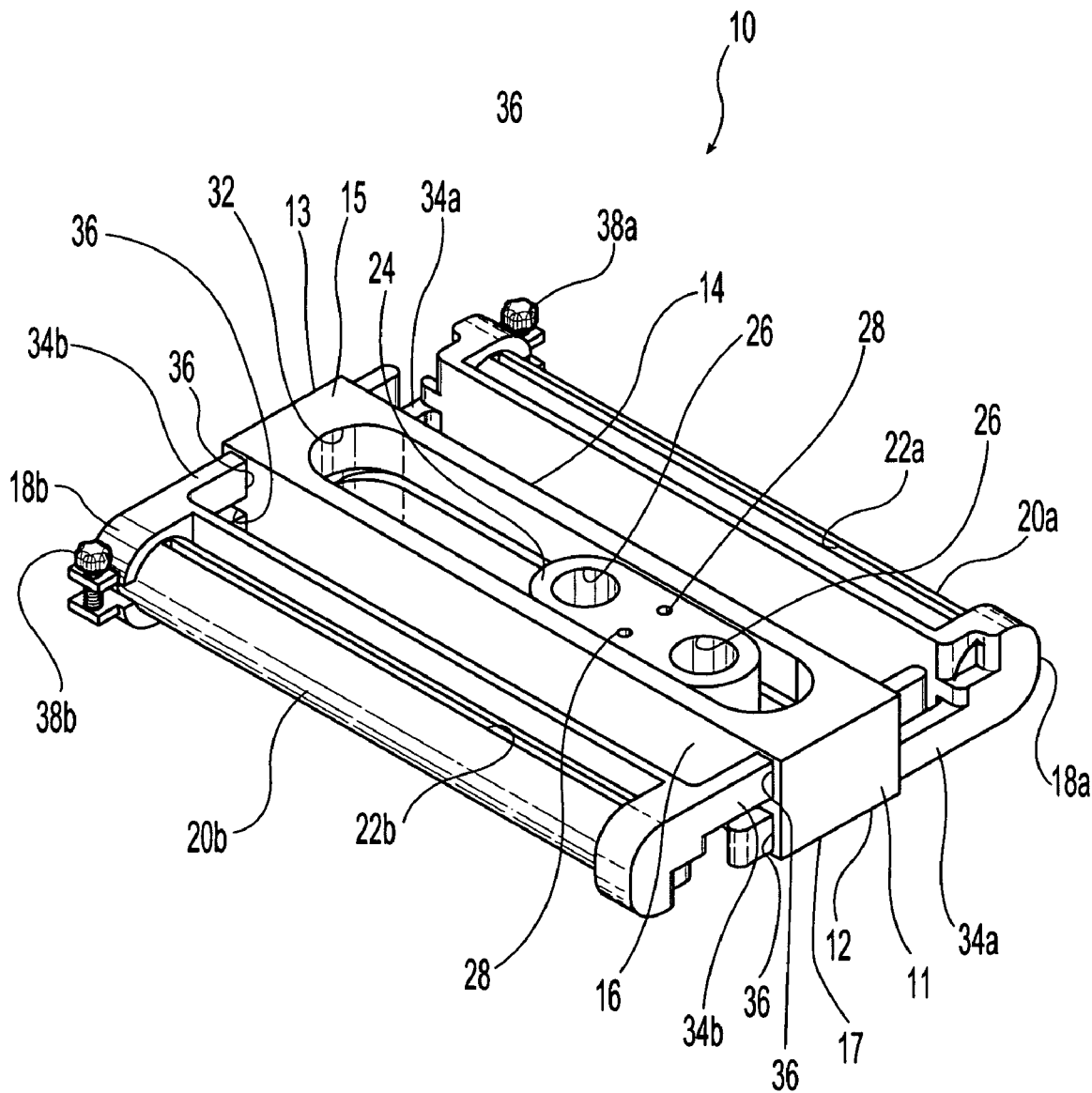
FIG. 1 is a top perspective view of an adjustable cut guide according to one embodiment of the present invention.
Figure 2:
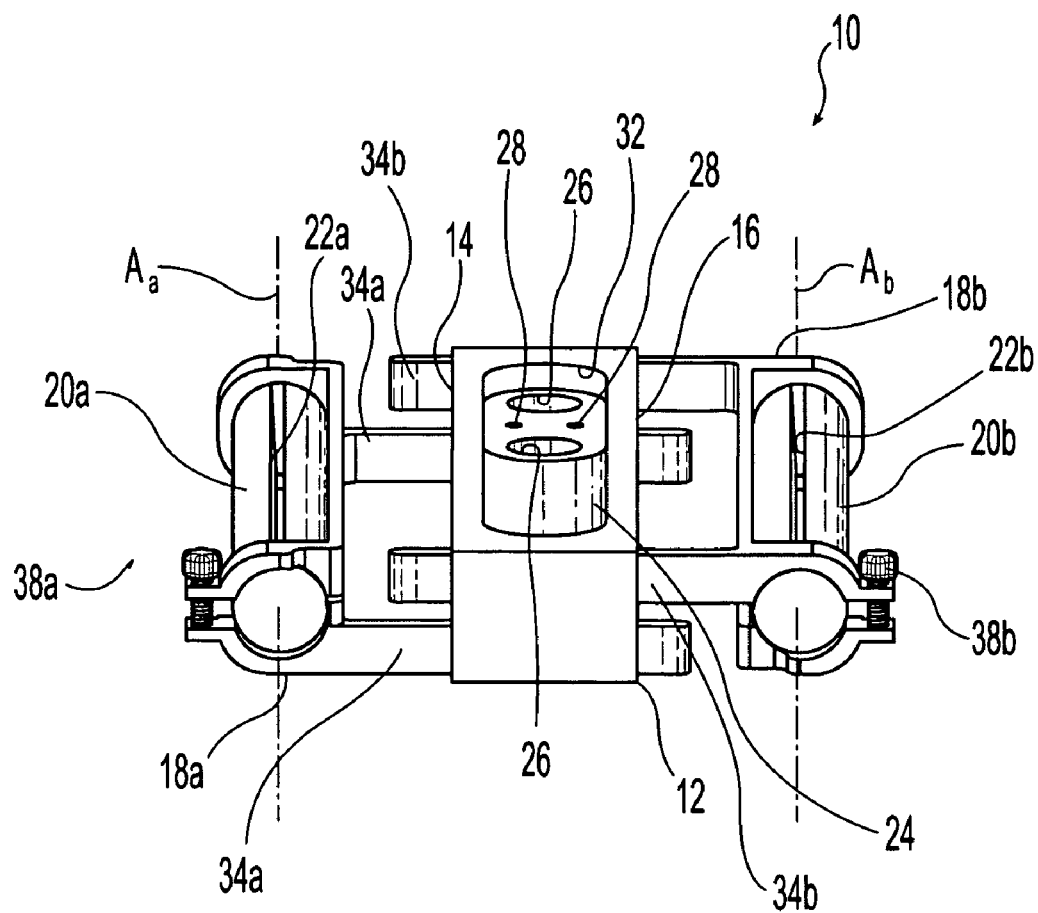
FIG. 2 is a side perspective view of the adjustable cut guide of FIG. 1.

Corresponding reference characters indicate corresponding parts throughout the several views. Although the drawings represent embodiments of the present invention, the drawings are not necessarily to scale and certain features may be exaggerated in order to better illustrate and explain the present invention. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments hereinafter disclosed are not intended to be exhaustive or limit the invention to the precise forms disclosed in the following description. Rather the embodiments are chosen and described so that others skilled in the art may utilize its teachings.

The present invention will now be described with reference to the attached figures. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase. Various anatomical reference terms used herein are intended to have the standard meaning for such terms as understood in the medical community. For example, the application may include reference to the following terms: anterior (the front, as opposed to the posterior); posterior (the back or behind, as opposed to the anterior); inferior (below, as opposed to superior); superior (above, as opposed to inferior); lateral (toward the left or right side of the body, as opposed to medial); medial (in the middle or inside, as opposed to lateral); proximal (toward the beginning, as opposed to distal); and distal (further from the beginning, as opposed to proximal).

Referring first to FIGS. 1-4, adjustable cut guide 10 according to one embodiment of the invention is illustrated. Cut guide 10 generally includes base 12, pair of guide housings 18a, 18b slideably coupled to opposite ends of base 12, and pair of guide members 20a, 20b rotatably coupled to respective guide housings 18a, 18b.

Figure 4:
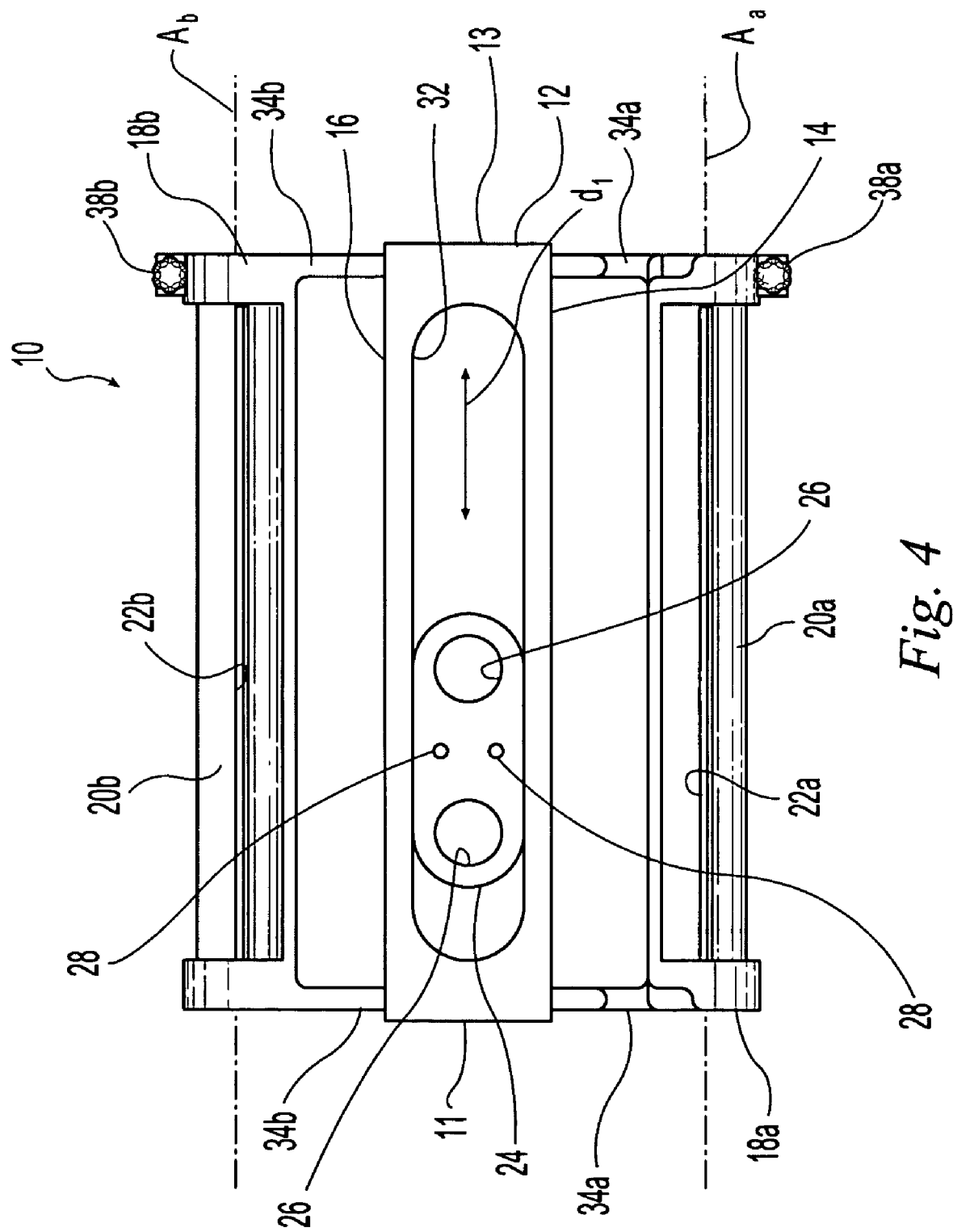
FIG. 4 is a top view of the adjustable cut guide of FIG. 1.
Figure 5:
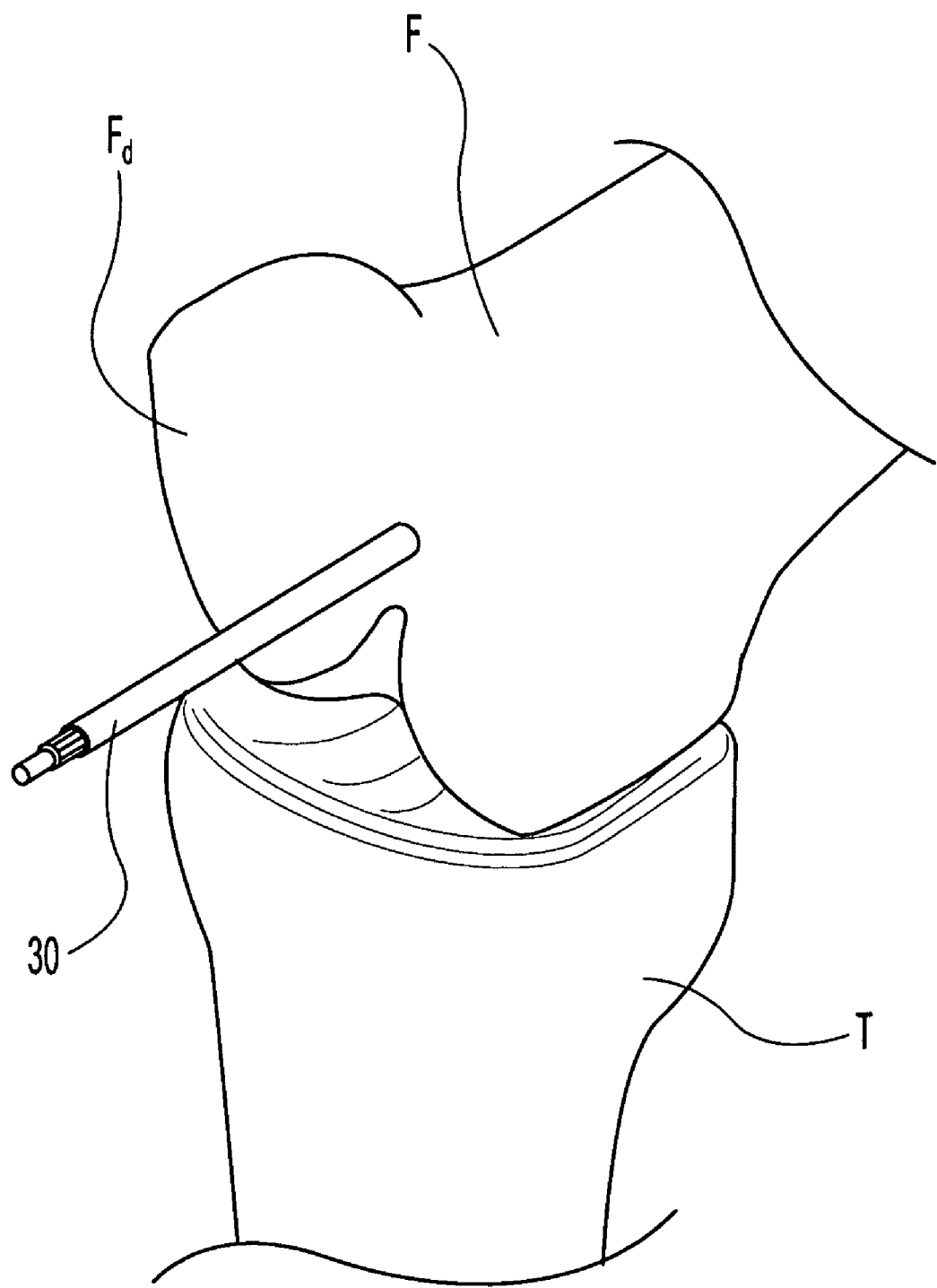
FIG. 5 is a medial perspective aspect of a knee joint wherein an intramedullary rod has been driven into the intramedullary canal of the femur.
Figure 6:
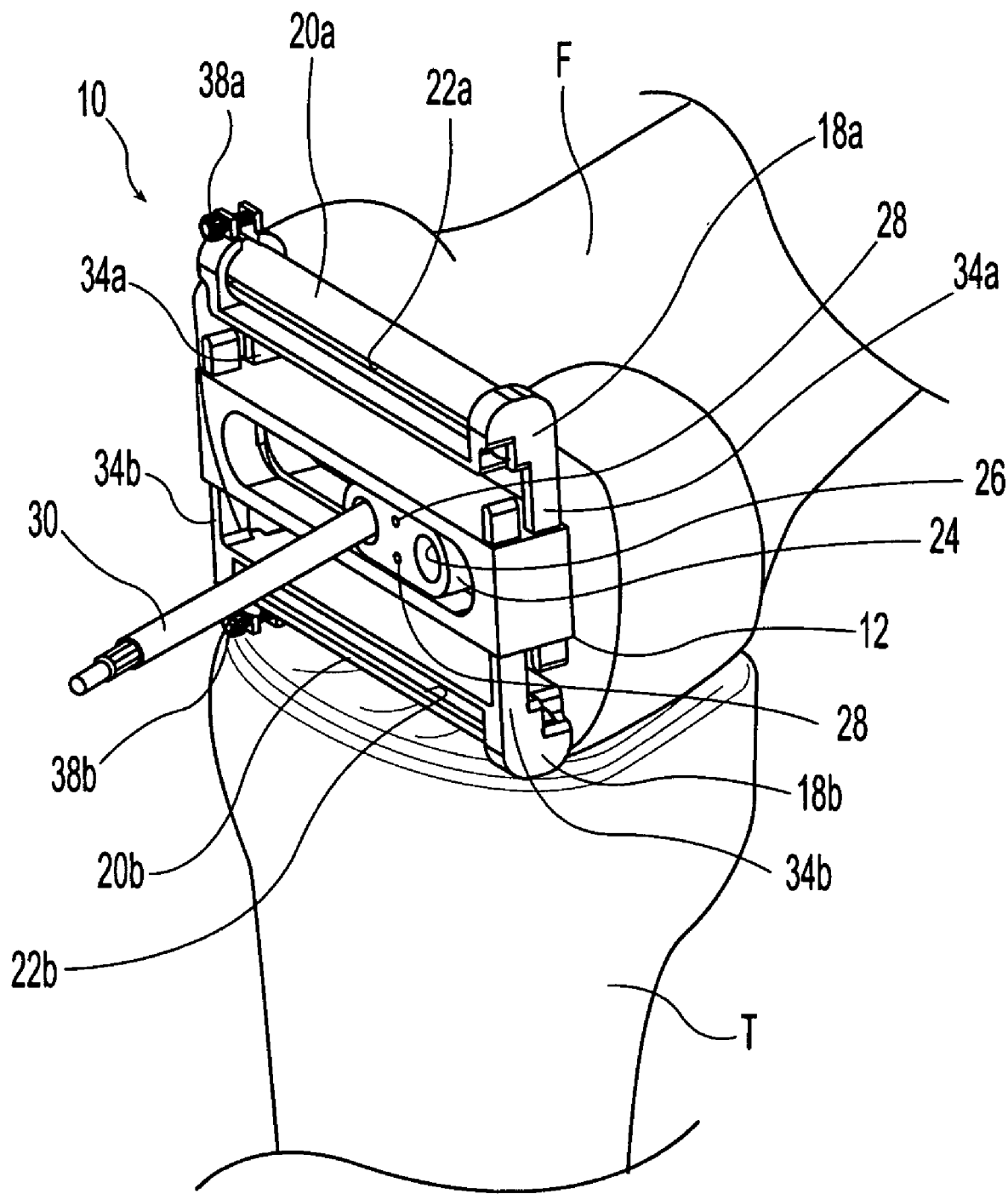
FIG. 6 is a medial perspective aspect of the knee joint of FIG. 5 wherein the adjustable cut guide of FIG. 1 is mounted on the intramedullary rod.

Base 12 is defined by opposing anterior and posterior ends 14, 16, opposing distal and proximal faces 15, 17, and opposing sides 11, 13. A pair of arm receiving openings 36 extend through base 12 from anterior end 14 to posterior end 16, and proximal each of opposing sides 11, 13. Base 12 includes elongated adapter slot 32, which extends through base 12 from distal face 15 to proximal face 17 and longitudinally between opposing sides 11, 13. Intramedullary (IM) rod adapter 24 is slideably disposed within adapter slot 32 and includes IM rod receiving openings 26 and fastener holes 28. IM rod adapter 24 is slideable within adapter slot 32 in the direction of double headed arrow $d_1$ (FIG. 4).

Referring still to FIGS. 1-4, pair of guide housings 18a, 18b are slideably coupled to base 12, and include anterior guide housing 18a disposed adjacent anterior end 14 of base 12 and posterior guide housing 18b disposed adjacent posterior end 16 of base 12. Each of anterior and posterior guide housings 18a, 18b includes pair of outwardly extending arms 34a, 34b, respectively. Arms 34a, 34b slideably extend through arm receiving openings 36 to, thereby, slideably couple guide housings 18a, 18b to base 12. Arms 34a, 34b may be adapted to manually slide within arm receiving openings 36 of body 12. Alternatively, cut guide 10 may include an adjustment apparatus adapted to affect the sliding of arms 34a, 34b within arm receiving openings 36. For instance, a rack and pinion or other gear-type adjustment apparatus may be used to slide arms 34a, 34b within arm receiving openings 36.

Figure 3:
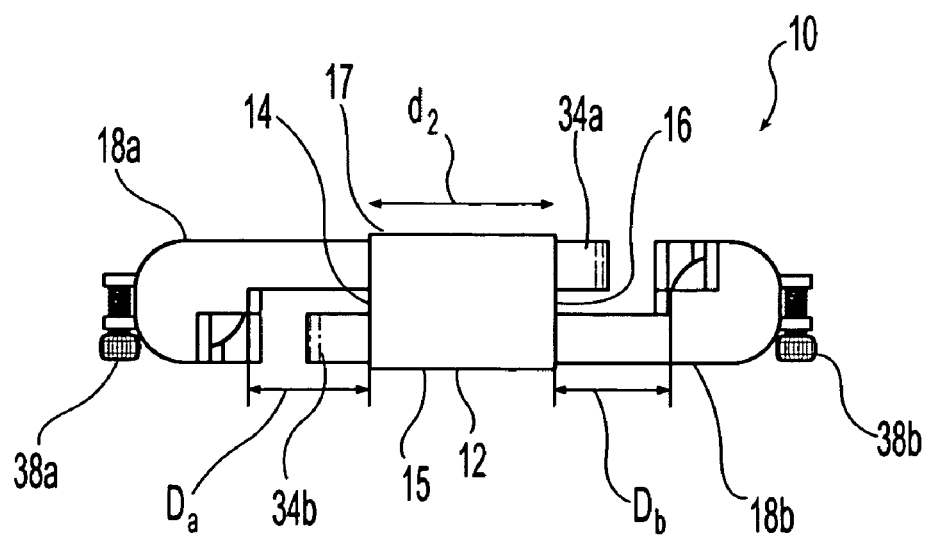
FIG. 3 is a side view of the adjustable cut guide of FIG. 1.

Referring specifically to FIG. 3, the slideable coupling of arms 34a, 34b to base 12 allows guide housings 18a, 18b to independently slide toward and away from base 12 in the direction of double-headed arrow $d_2$. As is discussed in further detail below, this independent sliding allows independent adjustment of both the distance $D_a$ between body 12 and guide member 20a, and distance $D_b$ between body 12 and guide member 20b.

Referring back to FIGS. 1-4, pair of guide members 20a, 20b include anterior guide member 20a and posterior guide member 20b, which are rotatably coupled to anterior and posterior guide housings 18a, 18b, respectively. In the illustrative drawings, the anterior and posterior guide members 20a, 20b are cylindrical in shape and define respective guide axes $A_a$, $A_b$ about which guide members 20a, 20b are rotatable. However, anterior and posterior guide members 20a, 20b can be any suitable shape and need not be cylindrical in shape. Anterior and posterior guide members 20a, 20b include respective anterior and posterior guide slots 22a, 22b, which extend therethrough and along guide axes $A_a$, $A_b$. As described further below, anterior and posterior guide slots 22a, 22b are each configured to receive therethrough and guide a saw such as a reciprocating bone saw.

Referring still to FIGS. 1-4, adjustable cut guide 10 also includes adjustment devices 38a, 38b. Adjustment devices 38a, 38b are operably engaged to guide members 20a, 20b, respectively and are adapted to rotate guide members 20a, 20b about respective axes $A_a$, $A_b$. The engagement between adjustment devices 38a, 38b and respective guide members 20a, 20b may be in any form that, upon movement of adjustment members 38a, 38b, would affect the rotation and/or lock the position of guide members 20a, 20b, respectively. For example, the engagement may be a "worm gear" type of engagement wherein adjustment devices 38a, 38b would include a knob at one end and a threaded portion (not shown) at the opposite end, the threads of which would engage the teeth of a gear (not shown) defined on the end of guide members 20a, 20b. Rotation of the knob of adjustment devices 38a, 38b, would cause the rotation of the threads which would, in turn, cause the rotation of the gear and of respective guide members 20a, 20b. Alternatively, the engagement between adjustment device 38a, 38b and guide members 20a, 20b may be a bevel gear mechanism. In yet another alternative, the adjustment device may be in the form of a lever (not shown) attached to the guide members. When pivoted, the lever would rotate the guide member.

In yet another form, guide members 20a, 20b may be coupled to respective guide housings 18a, 18b such that guide members 20a, 20b rotate freely about axes $A_a$, $A_b$. In this case, adjustment device 38a, 38b does not operate to rotate guide members 20a, 20b. Instead, adjustment device 38a, 38b is adapted to lock guide members 20a, 20b in position, thereby preventing rotation. For instance, adjustment device 38a, 38b may be adapted to work with guide housings 18a, 18b such that, when rotated, adjustment device 38a, 38b causes guide housings 18a, 18b to firmly grip guide members 20a, 20b, thereby restricting their free rotation.

The embodiments of the adjustment device described above are only exemplary and demonstrate that the engagement between adjustment device 38a, 38b and respective guide members 20a, 20b may take on a variety of forms. In addition, the embodiments described above and illustrated thus far show a separate adjustment device dedicated to each guide member. However, the present invention may be adapted to have a single adjustment device that affects the rotation and/or positioning of both guide members about their respective axes.

Turning now to FIGS. 5-8B, use of adjustable cut guide 10 will now be described. To prepare the distal end $F_d$ of femur F cut guide 10 may be used to guide the anterior and posterior cuts, as well as the chamfer cuts. First, the knee, which includes tibia T and femur F is positioned in approximately 90° flexion. Next, intramedullary (IM) rod 30 is driven into distal end $F_d$ of femur F. IM rod 30 may be installed using any procedure including, for instance, by first drilling a hole into distal end $F_d$ of femur F and inserting rod 30 into the hole. Cut guide 10 is mounted on distal end $F_d$ of femur F by inserting IM rod 30 into one of rod receiving openings 26 of IM rod adapter 24 and sliding rod adapter 24 down IM rod 30 until proximal face 17 of base 12 is seated against distal end of femur F. The installation of cut guide 10 on femur F may be performed before or after the distal cut is made.

Figure 7A:
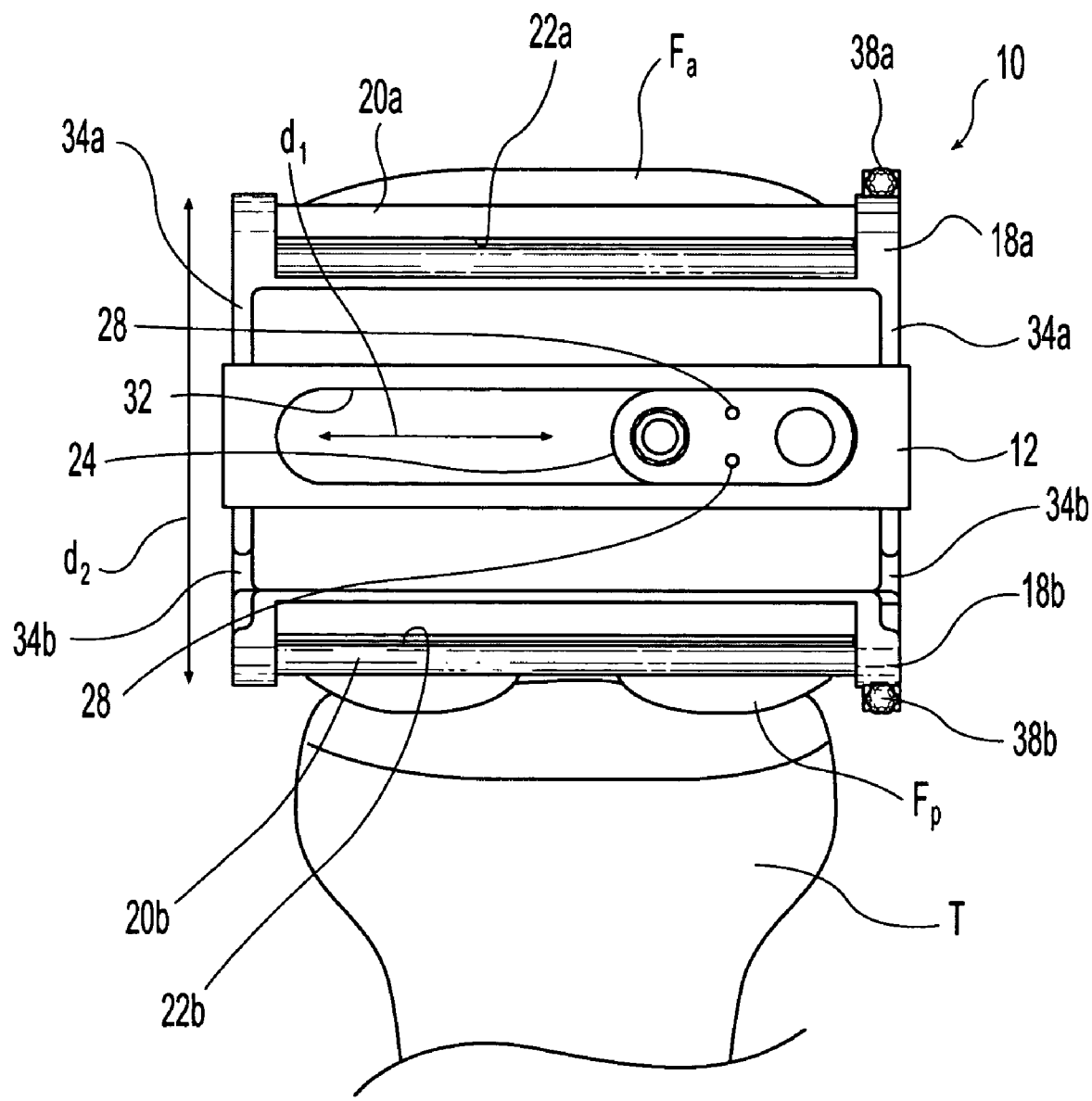
FIG. 7A is a distal end view of the knee and adjustable cut guide of FIG. 6 wherein the guide slots of the adjustable cut guide are positioned to guide the anterior and posterior cuts.

As shown in FIG. 7A, base 12 may then be rotated about the axis of IM rod 30 until anterior guide housing 18a and associated guide member 20 are aligned with and adjacent to anterior side $F_a$ of femur F. Once positioned, fasteners (not shown) may be inserted through fastener holes 28 and into distal end $F_d$ of femur F to secure position of IM rod adapter 24 and cut guide 10 about the axis of rod 30. Fasteners may be any suitable surgical fasteners including pins, nails and screws. Next, cut guide 10 may be positioned along plane/double-headed arrow $d_1$ by sliding base 12 along adapter 24, thereby positioning cut guide 10 to minimize interference by, and disruption of, soft tissue.

Assuming that the anterior and posterior cuts will be made prior to the chamfer cuts and referring to FIGS. 7A and 7B, guide slots 22a, 22b are positioned in alignment with desired cut lines $C_a$ and $C_p$, respectively. The position and angle of cut lines $C_a$ and $C_p$ may vary based on a number of factors including the size of the patient's femur, the size of implant, and the condition of the bone. The determination of cut lines $C_a$, $C_p$ and verification of alignment of guide slots 22a, 22b is discussed in further detail below. Referring still to FIGS. 7A and 7B, using adjustment devices 38a, 38b, guide members 20a, 20b are rotated and positioned such that the depth of guide slots 22a, 22b is aligned parallel with desired cut lines $C_a$, $C_p$, respectively.

Next, distances $D_a$ and $D_b$ (FIG. 3) may be adjusted to align guide slots 22a, 22b with cut lines $C_a$, $C_p$, respectively. Guide housings 18a, 18d are moved away from body 12 via the sliding of arms 34a, 34b within arm receiving openings 36 until guide slots 22a, 22b align with cut lines $C_a$, $C_p$, as illustrated in FIG. 7B. With cut guide 10 adjusted as shown in FIGS. 7A and 7B, saw S may be inserted through slots 22a, 22b to resect (cut) the desired amount of anterior and posterior portions of femur F.

Figure 8A:
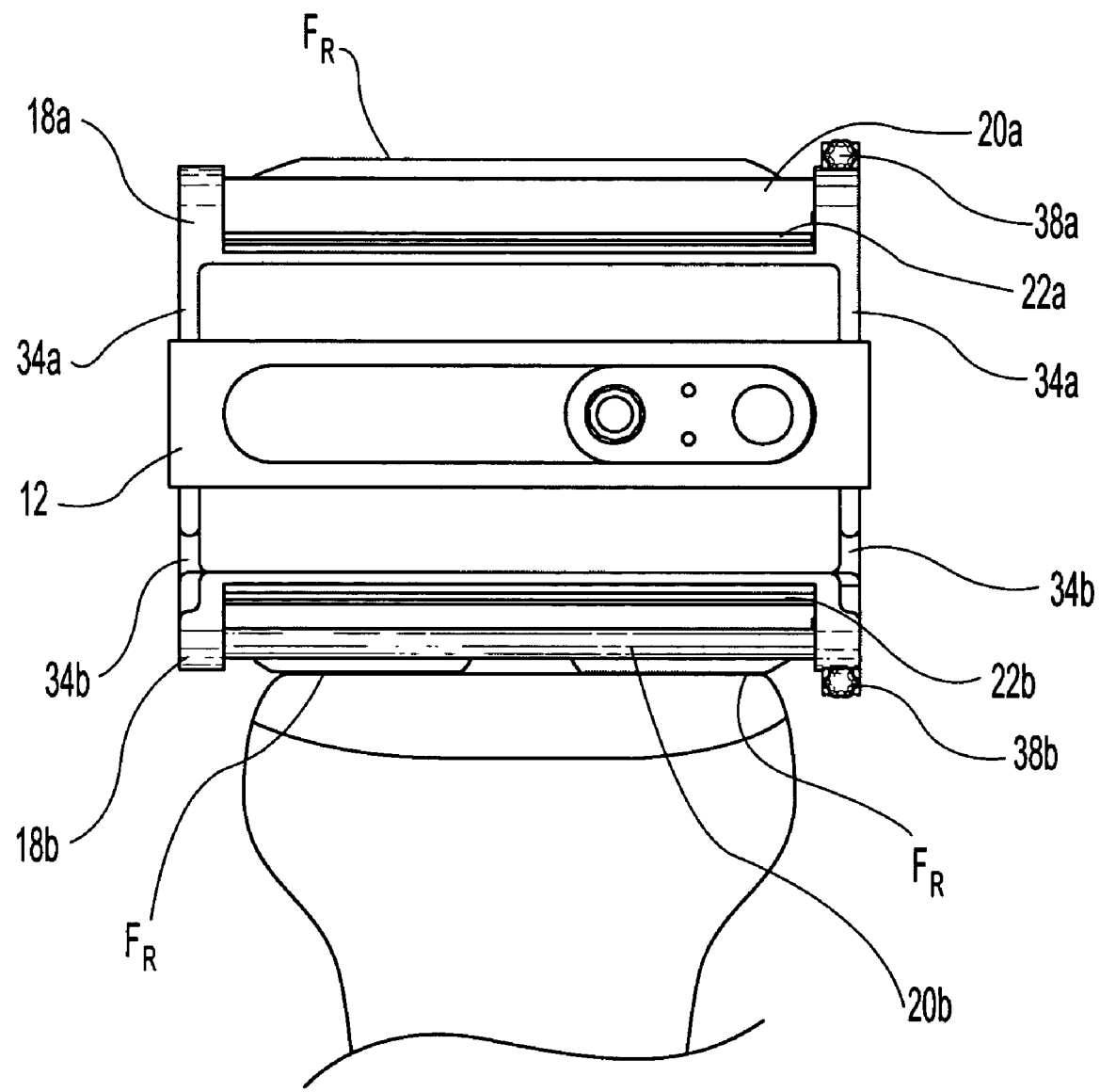
FIG. 8A is a distal end view of the knee and adjustable cut guide of FIG. 6 wherein the anterior and posterior cuts have been made and the guide slots of the adjustable cut guide are positioned to guide the anterior and posterior chamfer cuts.
Figure 8B:
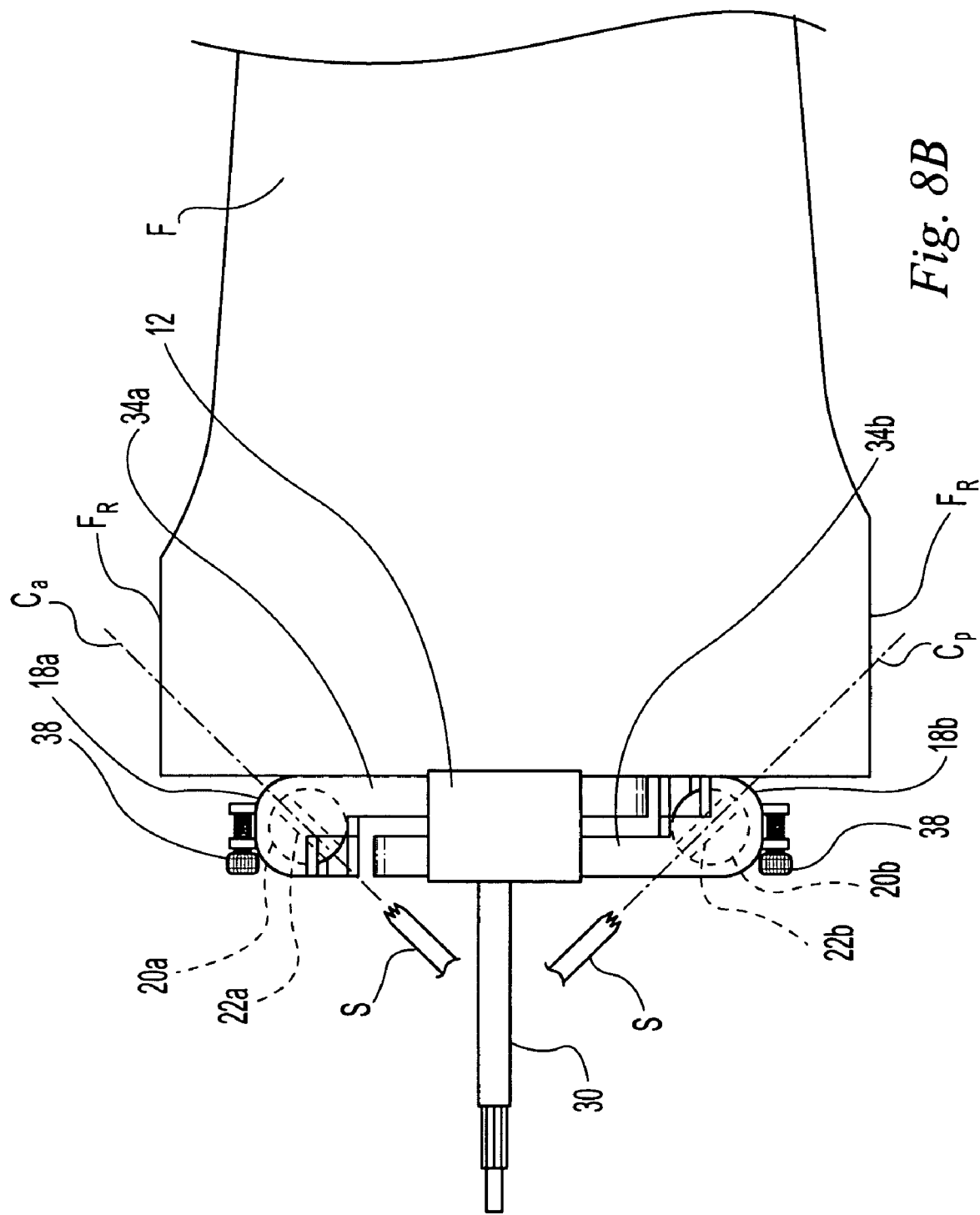
FIG. 8B is a side view of the knee and adjustable cut guide of FIG. 8A.

Turning to FIGS. 8A and 8B, anterior and posterior cuts yield femur F with resected anterior and posterior surfaces $F_R$. To make the anterior and posterior chamfer cuts, using adjustment device 38a, 38b, guide members 20a, 20b are rotated until guide slots 22a, 22b are at the appropriate angle, wherein the depth of guide slots 22a, 22b is parallel with desired chamfer cut lines $C_1$, $C_2$. Guide housings 18a, 18b are slid inward toward base 12 until guide slots 22a, 22b are aligned with desired chamfer cut lines $C_1$, $C_2$. With cut guide 10 in this position, saw S is inserted through slots 22a, 22b and cuts through the bone along chamfer lines $C_1$, $C_2$.

As noted above, the angle and position of desired cut lines $C_a$, $C_p$, $C_1$ and $C_2$ may depend upon a variety of factors including the size of femur, the size of selected femoral component, and the condition of the femur. To achieve proper anterior, posterior, and chamfer cuts, cut guide 10 may be adapted for use with computer navigational/computer assisted surgical systems. The cut lines may be mapped on a computer model of the femur. During surgery paddle devices may be inserted into slots 22a, 22b. Paddle devices may be viewed during surgery using computer assisted navigational technology and compared to the mapped model to determine when paddles and, therefore, slots 22a, 22b are aligned with the mapped cut lines.

To determine and verify proper alignment of slots 22a, 22b in manual surgical procedures, cut guide 10 may be equipped with visible indicators that indicate the position of guide slots 22a, 22b. For instance, arms 34a, 34b may include measurement markings or graduations (not shown) that correspond to certain sizes of implants. When aligned with a part of body 12, such as anterior or posterior ends 14, 16, the measurement markings indicate the appropriate position of guide housings. A similar marking mechanism may be incorporated on guide housings 18a, 18b. When aligned with slots 22a, 22b the markings would indicate the proper rotation of slots 22a, 22b.

Cut guide 10 may be formed of any surgical grade rigid material such as stainless steel. The components of cut guide 10, particularly base 12, guide housings 18a, 18b and guide members 20a, 20b may be formed of the same material or differing materials.

Although the embodiments illustrated and described above show an adjustable cut guide having both anterior and posterior guide housings and guide members, the cut guide of the present invention may be configured to have only a single guide housing and a single guide member. In this case, cut guide could be rotated about IM rod to position the cut guide for the anterior and posterior cuts. Furthermore, the present invention is illustrated through use in resecting the distal end of the femur. However, the cut guide may be adapted for use in resecting any bone.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An adjustable cut guide for use in resecting the end of a bone, the bone having an anterior side and a posterior side, the cut guide comprising:
    a base adapted to attach to the end of the bone, said base including an anterior end and an opposite posterior end;
    first and second guide housings coupled to said base and disposed adjacent said opposing anterior and posterior ends, respectively, of said base;
    anterior and posterior guide members rotatably coupled to said first and second guide housings, respectively, each of said anterior and posterior guide members rotatable about a guide axis and having an elongate guide slot extending along said guide axis and extending through said guide member in a direction transverse to said guide axis, whereby a cutting device guided through said elongate guide slot extends transverse to said guide axis, said anterior and said posterior guide members being rotatable about said guide axis to a first position in which said elongate guide slots are positioned in a first orientation and a second position in which said elongate guide slots are positioned in a second orientation, said first orientation of said elongate guide slots angled relative to said second orientation of said elongate guide slots, said first orientation of said elongate guide slots and said second orientation of said elongate guide slots being non-coincident;
    wherein when said base is attached to the end of the bone said anterior guide member is positioned proximal the anterior side of the bone and said posterior guide member is positioned proximal the posterior side of the bone.

2. The cut guide of claim 1 wherein each of said anterior and posterior guide members are cylindrical in shape.

3. The cut guide of claim 1 wherein said base includes an intramedullary rod adapter, said adapter having at least one rod opening.

4. The cut guide of claim 3 wherein said base includes an elongated adaptor slot, said adapter slideably disposed within said adapter slot.

5. The cut guide of claim 3 wherein said adapter includes at least one fastener receiving hole.

6. The cut guide of claim 1 wherein each of said guide housings is slideably coupled to said base such that a distance between each of said anterior and posterior guide members and said base member is adjustable.

7. The cut guide of claim 6 wherein each of said guide housings includes a pair of arms, said pair of arms slideably disposed within an arm receiving opening defined in said base.

8. The cut guide of claim 1 further including a guide member adjustment device associated with each of said anterior and posterior guide members, said adjustment device adapted to rotate corresponding one of said anterior and posterior guide members about said guide axis.

9. The cut guide of claim 1 wherein said elongate guide slot of each of said anterior and posterior guide members has a substantially rectangular cross section defined by a major dimension and a minor dimension, said major dimension extending along said guide axis and said minor dimension extending perpendicular to said guide axis.

10. An adjustable cut guide for use in resecting the end of a bone, the bone having an anterior side and a posterior side, the cut guide comprising:
a base adapted to attach to the end of the bone, said base including a first end and an opposite second end;
a guide housing coupled to said base and disposed adjacent said first end of said base, said guide housing including a cylindrical guide member defining a guide axis, said guide member rotatable about said guide axis and having an elongate guide slot extending along said guide axis and extending through said cylindrical guide member in a direction transverse to said guide axis, whereby a cutting device guided through said elongate guide slot extends transverse to said guide axis, said cylindrical guide member being rotatable about said guide axis to a first position in which said elongate guide slot is positioned in a first orientation and a second position in which said elongate guide slot is positioned in a second orientation, said first orientation of said elongate guide slot angled relative to said second orientation of said elongate guide slot, said first orientation of said elongate guide slot and said second orientation of said elongate guide slot being non-coincident;
wherein when said base is attached to the end of the bone said guide member is positionable proximal either one of the anterior and posterior sides of the bone.

11. The cut guide of claim 10 further comprising a second guide housing coupled to said base and disposed adjacent said second end of said base, said second guide housing including a second cylindrical guide member defining a second guide axis, said second guide axis being parallel to said guide axis, said second guide member rotatable about said second guide axis and having a second elongate guide slot extending therethrough along said second guide axis, and wherein when said base is attached to the end of the bone said second guide member is positioned proximal the other one of the anterior and posterior sides of the bone.

12. The cut guide of claim 11 wherein each of said guide housing and said second guide housing is slideably coupled to said base such that each of said guide housing and second guide housing slides along a plane and the distance between each of said guide members and said base is thereby adjustable, said plane being substantially perpendicular to said guide axis.

13. The cut guide of claim 11 further including first and second guide member adjustment devices adapted to rotate said guide member and said second guide member, respectively.

14. The cut guide of claim 11 further including a guide member adjustment device adapted to rotate said guide member and said second guide member.

15. The cut guide of claim 10 further including an intramedullary rod adapter having at least one rod opening.

16. The cut guide of claim 15 wherein said base includes an elongated adaptor slot, said adapter slideably disposed within said adapter slot.

17. The cut guide of claim 16 wherein said adapter includes at least one fastener receiving hole.

18. The cut guide of claim 10 wherein said guide housing is slideably coupled to said base such that said guide housing slides along a plane and the distance between said guide member and said base is thereby adjustable, said plane being substantially perpendicular to said guide axis.

19. The cut guide of claim 10 further including a guide member adjustment device adapted to rotate said guide member about said guide axis.

20. The cut guide of claim 10 wherein said elongate guide slot of said cylindrical guide member has a substantially rectangular cross section defined by a major dimension and a minor dimension, said major dimension, extending along said guide axis and said minor dimension extending perpendicular to said guide axis.

21. An adjustable cut guide for use in resecting the end of a bone, the bone having an anterior side and a posterior side, the cut guide comprising:
a base adapted to attach to the end of the bone, said base including an anterior end and an opposite posterior end;
first and second guide housings slideably coupled to said base and disposed adjacent said opposing anterior and posterior ends, respectively, of said base;
anterior and posterior guide members rotatably coupled to said first and second guide housings, respectively, each of said anterior and posterior guide members rotatable about a guide axis and having an elongate guide slot extending along said guide axis and extending through said guide member in a direction transverse to said guide axis, whereby a cutting device guided through said elongate guide slot extends transverse to said guide axis, said anterior and said posterior guide members being rotatable about said guide axis to a first position in which said elongate guide slots are positioned in a first orientation and a second position in which said elongate guide slots are positioned in a second orientation, said first orientation of said elongate guide slots angled relative to said second orientation of said elongate guide slots, said first orientation of said elongate guide slots and said second orientation of said elongate guide slots being non-coincident;
wherein when said base is attached to the end of the bone said anterior guide member is positioned proximal the anterior side of the bone and said posterior guide member is positioned proximal the posterior side of the bone, and wherein each of said guide housings is slideable relative to said base along a plane and the distance between each of said guide members and said base is thereby adjustable.

22. The cut guide of claim 21 wherein each of said anterior and posterior guide members includes a rotation adjustment device.

23. The cut guide of claim 21 wherein said elongate guide slot of each of said anterior and posterior guide members has a substantially rectangular cross section defined by a major dimension and a minor dimension, said major dimension extending along said guide axis and said minor dimension extending perpendicular to said guide axis.

* * * * *

UNITED STATES PATENT AND TRADEMARK OFFICE
CERTIFICATE OF CORRECTION

PATENT NO. : 7,621,920 B2 Page 1 of 1
APPLICATION NO. : 11/151062
DATED : November 24, 2009
INVENTOR(S) : Claypool et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 197 days.

Signed and Sealed this

Twenty-sixth Day of October, 2010

David J. Kappos
*Director of the United States Patent and Trademark Office*